United States Patent

Hell et al.

[11] 3,941,791
[45] Mar. 2, 1976

[54] COMPOUNDS OF THE NAPHTHALIMIDE SERIES

[75] Inventors: Renate Elisabeth Hell, Frankenthal; Horst Scheuermann, Ludwigshafen, both of Germany

[73] Assignee: BASF Aktiengesellschaft, Ludwigshafen (Rhine), Germany

[22] Filed: Sept. 18, 1974

[21] Appl. No.: 507,190

Related U.S. Application Data

[63] Continuation-in-part of Ser. No. 373,114, June 25, 1973, abandoned.

[30] Foreign Application Priority Data

June 28, 1972 Germany.......................... 2231609

[52] U.S. Cl. ...... 260/281 Q; 260/281 N; 106/288 Q
[51] Int. Cl.² ........................................ C07D 217/24
[58] Field of Search.................... 260/281 A, 281 N

[56] References Cited
UNITED STATES PATENTS

| | | | |
|---|---|---|---|
| 3,330,834 | 7/1967 | Kasai | 260/281 |
| 3,697,525 | 10/1972 | Okada | 260/281 |

FOREIGN PATENTS OR APPLICATIONS

| | | | |
|---|---|---|---|
| 45-03671 | 12/1967 | Japan | 260/281 |
| 45-34438 | 11/1967 | Japan | 260/281 |
| 45-00774 | 5/1967 | Japan | 260/281 |
| 46-38418 | 6/1968 | Japan | 260/281 |

OTHER PUBLICATIONS

Kasai et al. CA 72, 4500ld 1970.
Scheuerman et al. CA 78, 137970, 1972.
Hell et al., Chem. Abs. 80, 146979z (1974)(German 2231609).

*Primary Examiner*—Richard J. Gallagher
*Assistant Examiner*—Mark L. Berch
*Attorney, Agent, or Firm*—Johnston, Keil, Thompson & Shurtleff

[57] ABSTRACT

Naphthalimides of the formula

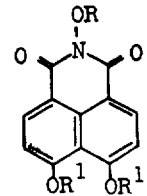

in which R and R¹ are hydrocarbon radicals. The compounds are eminently suitable for the optical brightening of synthetic fibers, particularly polyesters, on which outstanding brightening effects are obtained.

8 Claims, No Drawings

COMPOUNDS OF THE NAPHTHALIMIDE SERIES

This application is a continuation-in-part of our copending application Ser. No. 373,114, now abandoned filed June 25, 1973.

The invention relates to compounds of the formula I

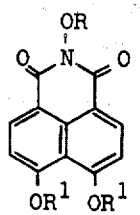

in which

R is alkyl of 1 to 18 carbon atoms, allyl, cycloalkyl of 5 to 8 carbon atoms, phenylalkyl of 1 to 4 carbon atoms in the alkyl, phenylalkyl substituted in the phenyl by chloro, methyl, ethyl, methoxy, carbomethoxy, carboethoxy or cyano and having 1 to 4 carbon atoms in the alkyl, hydroxyalkyl of 2 or 3 carbon atoms, alkoxyalkyl of 2 or 3 carbon atoms in the alkyl and 1 to 8 carbon atoms in the alkoxy, phenoxyalkyl of 2 to 3 carbon atoms in the alkyl, phenoxyalkyl substituted by chloro, methyl or methoxy and of 2 or 3 carbon atoms in the alkyl, cyanoethyl, chloroethyl, bromoethyl, chloropropyl, bromopropyl, alkoxycarbonylethyl of 1 to 8 carbon atoms in the alkoxy, β-carbamoylethyl, alkoxycarbonylmethyl of 1 to 8 carbon atoms in the alkoxy, alkanoyloxyalkyl of 1 to 18 carbon atoms in the alkanoyl and 2 or 3 carbon atoms in the alkyl, alkanoyloxyalkyl of 2 to 4 carbon atoms in the alkanoyl, 2 or 3 carbon atoms in the alkyl and substituted in the alkanoyl by chloro, bromo, hydroxy, methoxy, ethoxy, phenoxy or phenyl, cyclohexylcarbonyloxyalkyl of 2 to 3 carbon atoms in the alkyl, benzoyloxyalkyl or benzoyloxyalkyl substituted in the phenyl ring by chloro, methyl or methoxy and having 2 or 3 carbon atoms in the alkyl, alkoxycarbonyloxyalkyl of 1 to 8 carbon atoms in the alkoxy and 2 or 3 carbon atoms in the alkyl, β-alkoxy-ethoxycarbonyloxyalkyl of 1 to 4 carbon atoms in the β-alkoxy and 2 or 3 carbon atoms in the alkyl, cyclohexoxycarbonyloxyalkyl, benzyloxycarbonyloxyalkyl, β-phenylethoxycarbonyloxyalkyl, phenoxycarbonyloxyalkyl or phenoxycarbonyloxyalkyl substituted in the phenoxy by chloro, methyl or methoxy, the alkyl having 2 or 3 carbon atoms in each case, alkylaminocarbonyloxyalkyl of 1 to 8 carbon atoms in the alkylamino and 2 or 3 carbon atoms in the alkyl, phenylaminocarbonyloxyalkyl or phenylaminocarbonyloxyalkyl substituted in the phenyl by chloro or methyl and having 2 or 3 carbon atoms in the alkyl,

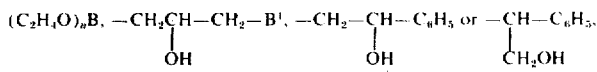

n is 2, 3 or 4,

B is hydrogen or alkyl of 1 to 4 carbon atoms,

B¹ is hydroxy, alkoxy of 1 to 8 carbon atoms, β-alkoxyethoxy of 1 to 4 carbon atoms in the alkoxy, phenoxy, phenoxy substituted by chloro, methyl or methoxy, phenylmercapto or methoxyphenylmercapto, and R¹ is alkyl of 1 to 6 carbon atoms, hydroxyalkyl of 2 to 6 carbon atoms, alkoxyalkyl of 1 to 4 carbon atoms in the alkoxy and 2 to 6 carbon atoms in the alkyl or $(CH_2CH_2O)_nB$.

Specific radicals R apart from those already named are: methyl, ethyl, propyl, butyl, pentyl, hexyl, heptyl, octyl, β-ethylhexyl nonyl, decyl, undecyl, dodecyl, tetradecyl, hexadecyl, octadecyl, cyclopentyl, cyclohexyl, methylcyclohexyl, cycloheptyl, norbornyl, cyclooctyl, benzyl, phenylethyl, phenylpropyl, phenylbutyl, chlorobenzyl, methylbenzyl, dimethylbenzyl, methoxybenzyl, carbomethoxybenzyl, cyanobenzyl, cyanophenylethyl, β-hydroxyethyl or -propyl, β,γ-dihydroxypropyl, β-methoxyethyl, β-ethoxy-, β-propoxy-, β-butoxy-, β-pentoxy-, β-hexoxy-, β-(β-ethylhexoxy)-, β-octoxy-ethyl or -propyl, β-phenoxyethyl or -propyl, chloro-phenoxy-, methylphenoxy- or methoxyphenoxyethyl or -propyl, methoxycarbonylethyl, ethoxy-, propoxy-, butoxy-, hexoxy-, β-ethylhexoxy- or octoxycarbonyl-ethyl or -methyl, formyloxyethyl, acetoxy-, propionyloxy-, butyryloxy-, hexanoxyloxy-, β-ethylhexanoyloxy-, decanoyloxy-, dodecanoyloxy-, hexadecanoyloxy- or octadecanoyloxy-ethyl or -propyl, chloroacetoxyethyl, bromo-, hydroxy-, methoxy-, ethoxy-, phenoxy- or phenylacetoxyethyl or -propyl, β-chloropropionyloxy-ethyl or -propyl, γ-chlorobutyryloxyethyl or -propyl, methoxycarbonyloxyethyl, ethoxy-, propoxy-, butoxy-, hexoxy-, β-ethylhexoxy- or octoxycarbonyloxy-ethyl or -propyl, β-methoxyethoxycarbonyloxy-ethyl or -propyl, β-butoxyethoxycarbonyloxy-ethyl or -propyl, methylaminocarbonyloxyethyl, propyl-, butyl-, hexyl-, β-ethylhexyl- or octylaminocarbonyloxy-ethyl or -propyl,

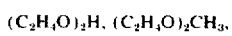

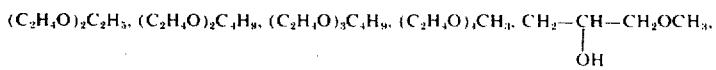

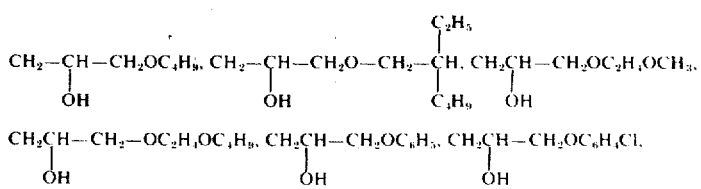

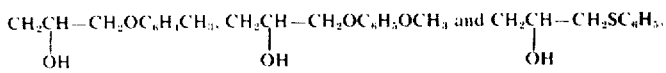

Preferred radicals R are: alkyl of 1 to 12 carbon atoms, hydroxyalkyl of 2 or 3 carbon atoms, alkoxyalkyl of 1 to 4 carbon atoms in the alkoxy and 2 or 3 carbon atoms in the alkyl, cyclohexyl, benzyl, benzyl substituted by cyano, carbomethoxy or carboethoxy, phenylethyl, phenylpropyl, $(C_2H_4O)_nB$ or

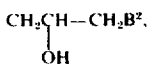

where $B^2$ is hydroxy, alkoxy of 1 to 6 carbon atoms, β-alkoxyethoxy of 1 to 4 carbon atoms in the alkoxy or phenoxy and B and n have the meanings given above.

Specific radicals $R^1$ are methyl, ethyl, propyl, butyl, pentyl, hexyl, β-hydroxyethyl or -propyl, ω-hydroxybutyl, ω-hydroxypentyl, ω-hydroxyhexyl, βmethoxyethyl, β-ethoxy-, β-propoxy- and β-butoxyethyl or -propyl, ω-methoxybutyl, ω-methoxyhexyl, $(CH_2CH_2O)_2CH_3$, $(CH_2CH_2O)_2C_2H_5$, $(CH_2CH_2O)_2C_4H_9$, $(CH_2CH_2O)_3CH_3$ and $(CH_2CH_2O)_4CH_3$.

Preferred radicals $R^1$ are alkyl of 1 to 6 carbon atoms or alkoxyethyl of 1 to 4 carbon atoms in the alkoxy.

It will be understood that references to propyl, butyl, etc. include the isomeric radicals such as isopropyl and isobutyl.

Compounds of the formula I may be prepared by the following reactions:

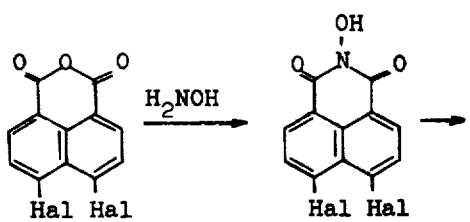

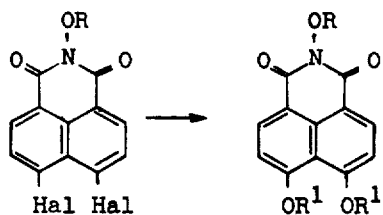

where Hal is bromine or preferably chlorine.

The 4,5-dichloronaphthalic acid anhydride is known from the literature (see e.g. M. M. Daschewski and G. T. Petrenko, Ukranian Chemical Journal, 21, Volume 3 (1955), pages 370 to 721) and is prepared by halogenation and subsequent oxidation from acenaphthene.

Many compounds of the formula (I) may also be prepared by reacting a compound of the formula (II):

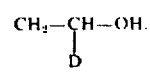

(II)

with an epoxide of the formula (III):

$$H_2C\underset{O}{\overset{D}{-}}CH$$ (III)

in which D is hydrogen, methyl or phenyl in an alcohol of the formula:

$$R^1\text{-OH}$$

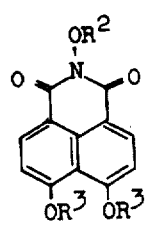

and converting the radical $$CH_2-CH-OH$$
$$\quad\quad\;|$$
$$\quad\quad\;D$$

into a radical R.

It is surprising that in the reaction of the compound of the formula (II) with a large (more than 100%) excess of epoxide of the formula (III) in an alcohol of the formula $R^1$—OH often exchange of the halogen for $OR^1$ takes place simultaneously with the introduction of the radical $$CH_2-CH-OH.$$
$$\quad\quad\;|$$
$$\quad\quad\;D$$

The reactions are known in principle and proceed analogously under comparable conditions. Details are given in the Examples.

Of particular importance industrially are compounds of the formula Ia wherein

R² is alkyl of 1 to 8 carbon atoms, β-hydroxyethyl, β-hydroxypropyl, β-alkoxyethyl of 1 to 4 carbon atoms in the alkoxy, β-chloroethyl, cyclohexyl or $(C_2H_4O)_2B$, and R³ is alkyl of 1 to 6 carbon atoms, B having the meanings given above.

The compounds of formula I are colorless to pale yellow and are suitable as optical brighteners for example for synthetic fibers such as polyamides, cellulose esters, acrylonitrile polymers and particularly polyesters.

The brightened fibers have very good lightfastness and washfastness. The compounds have a very pronounced whitening effect and high color strength.

The following Examples illustrate the invention. Parts and percentages are by weight unless otherwise stated.

EXAMPLE 1

28.2 Parts of 4,5-dichloro-N-hydroxynaphthalimide is dissolved in 1100 parts of methanol and 120 parts of triethylamine with heating under reflux. The solution is filtered, 54.5 parts of ethyl bromide is added and the whole is heated under reflux for 3½ hours. After another 54.5 parts of ethyl bromide has been added, the whole is heated for another hour and the precipitated product is suction filtered and washed with methanol. 24 Parts (78% of theory) of 4,5-dichloro-N-ethoxynaphthalimide is obtained having a melting point of 197° to 199°C.

18.6 Parts of the naphthalimide thus obtained, 43 parts of 30% sodium methoxide solution and 250 parts of methanol are heated under reflux for 4 hours. After the whole has cooled it is suction filtered and washed with methanol and water. 14 Parts (77% of theory) of 4,5-dimethoxy-N-ethoxynaphthalimide is obtained having a melting point of 230° to 232°C. The compound melts at 232° to 233°C after it has been recrystallized from methyl glycol.

When the ethyl bromide in Example 1 is replaced by n-butyl bromide (Example 2) and benzyl chloride (Example 3), the following compounds are obtained:

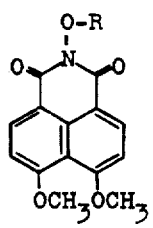

| Example No. | R | Melting point |
|---|---|---|
| 2 | n-C₄H₉ | 220° to 222°C |
| 3 | CH₂—C₆H₅ | 269° to 270°C |

EXAMPLE 4

28.2 Parts of 4,5-dichloro-N-hydroxynaphthalimide is dissolved in 350 parts of methanol, 350 parts of water and 40 parts of triethylamine with heating under reflux. 30 Minutes later 32 parts of hexylbromide is added during 4 hours. After 3 hours stirring at 65° to 70°C the whole is allowed to cool, suction filtered and dried. 35 Parts of 4,5-dichloro-N-hexoxynaphthalimide is obtained, having a melting point of 123° to 126°C.

35 Parts of the naphthalimide thus obtained, 520 parts of methanol and 85 parts of 30% sodium methoxide solution are heated under reflux for 5 hours. After the whole has cooled it is suction filtered and washed with water. 29 parts of N-hexoxy-4,5-dimethoxynaphthalimide is obtained having a melting point of 191° to 195°C. The compound melts at 195° to 197°C after recrystallization from toluene.

EXAMPLE 5

28.2 Parts of 4,5-dichloro-N-hydroxynaphthalimide is dissolved in 120 parts of triethylamine and 1100 parts of methanol at 60°C. Insoluble matter is filtered off and 22 parts of ethylene oxide is passed in at refluxing temperature. The mixture is heated for another 8 hours, allowed to cool, suction filtered and washed with methanol. 17 parts (54% of theory) of 4,5-dimethoxy-N-β-hydroxyethoxynaphthalimide is obtained having a melting point of 242° to 243°C. A sample recrystallized from chlorobenzene has the same melting point.

EXAMPLE 6

The ethylene oxide in Example 5 is replaced by propylene oxide. After the product has been recrystallized from o-dichlorobenzene, 12 parts (36% of theory) of 4,5-dimethoxy-N-β-hydroxypropoxynaphthalimide is obtained having a melting point of 250° to 252°C.

EXAMPLE 7

Analogously to Example 5 a mixture of compounds of the formulae:

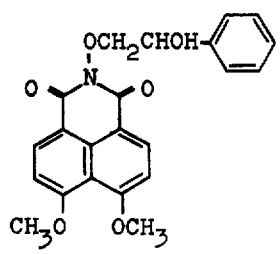

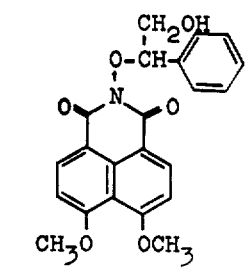

is obtained in a yield of 51% from 4,5-dichloro-N-hydroxynaphthalimide and styrene oxide. The mixture melts at 236° to 238°C after it has been recrystallized from glacial acetic acid.

EXAMPLE 8

16 Parts of 4,5-dimethoxy-N-β-hydroxyethoxynaphthalimide is suspended in 160 parts of chlorobenzene and then 12 parts of thionyl chloride and 0.5 parts of dimethylformamide are added. The mixture is stirred for 11 hours under reflux; after cooling, the reaction product is suction filtered and washed with petroleum ether. 16 parts (96% of theory) of pale yellow crystals is obtained having a melting point of 258° to 259°C. The compound has the formula:

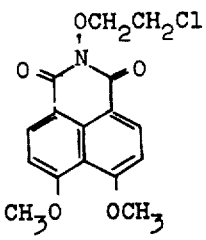

EXAMPLE 9

15.5 Parts of 4,5-dimethoxy-N-β-hydroxyethoxynaphthalimide and 7 parts of potassium carbonate are suspended in 100 parts of chlorobenzene and 8 parts of acetyl chloride is added. The whole is stirred for 15 hours at 85°C and then the product is precipitated with petroleum ether, suction filtered and stirred in 300 parts of water. 17 parts (95% of theory) of 4,5-dimethoxy-N-β-acetoxyethoxynaphthalimide is obtained having a melting point of 193° to 195°C.

EXAMPLE 10

The acetyl chloride in Example 9 is replaced by ethyl chloroformate. The compound of the formula:

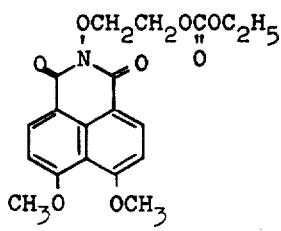

is obtained in a yield of 86%; it melts at 241° to 243°C.

EXAMPLE 11

15 Parts of 4,5-dimethoxy-N-β-hydroxyethoxynaphthalimide is suspended in 150 parts of chlorobenzene and 10 parts of phenyl isocyanate is added. The mixture is stirred for 20 hours at 80°C. The product is suction filtered and recrystallized from acetic acid. 17 parts (86% of theory) of the compound of the formula:

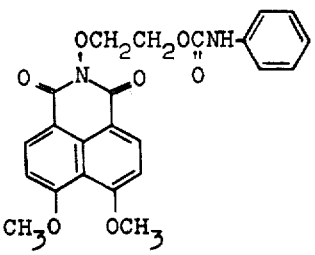

is obtained having a melting point of 253° to 255°C.

EXAMPLE 12

56.4 Parts of 4,5-dichloro-N-hydroxynaphthalimide is dissolved in 700 parts of water, 650 parts of methanol and 80 parts of triethylamine with heating under reflux. After 30 minutes 70 parts of n-heptyl bromide is added within 4 hours. After three hours stirring at 65° to 70°C the whole is allowed to cool, suction filtered and dried. 70 parts of N-heptoxy-4,5-dichloronaphthalimide is obtained having a melting point of 135° to 137°C.

70 Parts of the naphthalimide thus obtained, 1000 parts of methanol and 170 parts of sodium methoxide solution (30%) are heated under reflux for 5 hours. After the whole has cooled, it is suction filtered and washed with water. 60 Parts of N-heptoxy-4,5-dimethoxynaphthalimide is obtained. The compound melts at 180° to 182°C after recrystallization from toluene.

EXAMPLE 13

When the heptyl bromide in Example 12 is replaced by 2-ethylhexylbromide, N-(2-ethyl-hexoxy)-4,5-dimethoxy-naphthalimide is obtained. The compound melts at 218° to 220°C after it has been recrystallized from butyl acetate.

EXAMPLE 14

110 Parts of N-ethoxy-4,5-dichloronaphthalimide, 900 parts of butanol and 670 parts of potassium butoxide (26%) are heated at 80°C for 10 hours. After the whole has cooled, 900 parts of methanol is added. The precipitated product is suction filtered and washed with water. 80 parts of N-ethoxy-4,5dibutoxynaphthalimide is obtained having a melting point of 219° to 221°C.

EXAMPLE 15

When the N-ethoxy-4,5-dichloronaphthalimide in Example 14 is replaced by N-butoxy-4,5-dichloronaphthalimide, N-butoxy-4,5-dibutoxynaphthalimide is obtained. The compound melts at 198° to 200°C after it has been recrystallized from butyl acetate.

The compounds identified in the following table are obtained analogously to the methods described above.

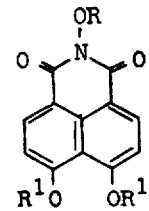

| Example | R | $R^1$ | Fluorescence in ethanol |
|---|---|---|---|
| 16 | $CH_3$ | $C_2H_5$ | blue violet |
| 17 | $C_2H_5$ | $C_3H_7$ | blue violet |
| 18 | $C_3H_7$ | $C_2H_5$ | blue violet |
| 19 | $C_4H_9$ | $C_2H_5$ | blue violet |
| 20 | $C_5H_{11}$ | $C_2H_5$ | blue violet |

-continued

| Example | R | R¹ | Fluorescence in ethanol |
|---|---|---|---|
| 21 | $C_5H_{11}$ | $CH_3$ | violet |
| 22 | $C_6H_{13}$ | $C_2H_5$ | blue violet |
| 23 | $C_6H_{13}$ | $C_4H_9$ | blue violet |
| 24 | $C_7H_{15}$ | $C_3H_7$ | blue violet |
| 25 | $C_8H_{17}$ | $C_2H_5$ | blue violet |
| 26 | $C_8H_{17}$ | $CH_3$ | violet |
| 27 | $C_9H_{19}$ | $CH_3$ | violet |
| 28 | $C_{10}H_{21}$ | $CH_3$ | violet |
| 29 | $C_{11}H_{23}$ | $CH_3$ | violet |
| 30 | $C_{12}H_{25}$ | $CH_3$ | violet |
| 31 | $C_{14}H_{29}$ | $CH_3$ | violet |
| 32 | $C_{15}H_{31}$ | $C_2H_5$ | blue violet |
| 33 | $C_{16}H_{37}$ | $CH_3$ | violet |
| 34 | $C_{17}H_{35}$ | $CH_3$ | violet |
| 35 |  | $CH_3$ | violet |
| 36 |  | $C_2H_5$ | blue violet |
| 37 |  | $CH_3$ | violet |
| 38 |  | $C_2H_5$ | blue violet |
| 39 |  | $CH_3$ | violet |
| 40 | $CH_2-C_6H_5$ | $C_4H_9$ | blue violet |
| 41 | $C_2H_4-C_6H_5$ | $C_2H_5$ | blue violet |
| 42 | $C_3H_6-C_6H_5$ | $CH_3$ | violet |
| 43 | $C_4H_8-C_6H_5$ | $CH_3$ | violet |
| 44 | $CH_2-C_6H_4Cl$ | $CH_3$ | violet |
| 45 | $CH_2-C_6H_4CH_3$ | $CH_3$ | violet |
| 46 | $CH_2-C_6H_4OCH_3$ | $CH_3$ | violet |
| 47 | $CH_2-C_6H_4COOCH_3$ | $C_5H_9$ | blue violet |
| 48 | $CH_2-C_6H_4CN$ | $C_6H_{13}$ | blue violet |
| 49 | $C_2H_4C_6H_4CN$ | $C_2H_4OH$ | blue |
| 50 | $C_2H_4OH$ | $C_3H_5$ | blue violet |
| 51 | $C_3H_6OH$ | $C_2H_5$ | blue violet |
| 52 | $CH_2CHOH-CH_2OH$ | $CH_3$ | blue violet |
| 53 | $C_2H_4OCH_3$ | $CH_3$ | blue violet |
| 54 | $C_2H_4OC_2H_5$ | $C_4H_9$ | blue violet |
| 55 | $C_2H_4OC_3H_7$ | $C_3H_6OH$ | blue |
| 56 | $C_2H_4OC_4H_9$ | $C_6H_{11}OH$ | blue |
| 57 | $C_2H_4OC_5H_{11}$ | $C_2H_5OCH_3$ | blue |
| 58 | $C_3H_6OC_6H_{13}$ | $C_2H_5OC_2H_5$ | blue |
| 59 | $C_3H_6OC_8H_{17}$ | $C_2H_5OC_4H_9$ | blue |
| 60 | $C_2H_4OC_6H_5$ | $CH_3$ | blue violet |
| 61 | $C_3H_6OC_6H_5$ | $C_2H_5$ | blue violet |
| 62 | $C_2H_4OC_6H_4Cl$ | $C_4H_9$ | blue violet |
| 63 | $C_2H_4OC_6H_4CH_3$ | $C_2H_5$ | blue violet |
| 64 | $C_3H_6OC_6H_4OCH_3$ | $CH_3$ | blue violet |
| 65 | $C_2H_4COOCH_3$ | $CH_3$ | violet |
| 66 | $C_2H_4COOC_2H_5$ | $C_2H_5$ | blue violet |
| 67 | $C_2H_4COOC_3H_7$ | $C_3H_7$ | blue violet |
| 68 | $C_2H_4COOC_4H_9$ | $C_4H_9$ | blue violet |
| 69 | $C_2H_4COOC_6H_{13}$ | $CH_3$ | violet |
| 70 | $C_2H_4COOC_8H_{17}$ | $C_2H_5$ | blue violet |
| 71 | $CH_2-COOCH_3$ | $CH_3$ | violet |
| 72 | $CH_2-COOC_4H_9$ | $C_2H_5$ | blue violet |
| 73 | $CH_2-COOC_6H_{13}$ | $C_4H_9$ | blue violet |
| 74 | $C_2H_4OCHO$ | $CH_3$ | violet |
| 75 | $C_2H_4OCOCH_3$ | $C_2H_5$ | blue violet |
| 76 | $C_2H_4OCOC_2H_5$ | $C_3H_7$ | blue violet |
| 77 | $C_2H_4OCOC_3H_7$ | $CH_3$ | violet |
| 78 | $C_2H_4OCOC_5H_{11}$ | $CH_3$ | violet |
| 79 | $C_2H_4OCOC_6H_{13}$ | $C_2H_5$ | blue violet |
| 80 | $C_2H_4OCOC_8H_{19}$ | $CH_3$ | violet |
| 81 | $C_2H_4OCOC_{11}H_{23}$ | $CH_3$ | violet |
| 82 | $C_2H_4OCOC_{12}H_{25}$ | $CH_3$ | violet |
| 83 | $C_3H_6OCOC_{15}H_{31}$ | $CH_3$ | violet |
| 84 | $C_3H_6OCOC_7H_{15}$ | $CH_3$ | violet |
| 85 | $C_3H_6OCOCH_3$ | $CH_3$ | violet |
| 86 | $C_2H_4OCOC_{17}H_{35}$ | $CH_3$ | violet |
| 87 | $C_2H_4OCOCH_2Cl$ | $C_2H_5$ | violet |
| 88 | $C_2H_4OCOCH_2Br$ | $C_4H_9$ | blue violet |
| 89 | $C_2H_4OCOCH_2OH$ | $CH_3$ | violet |
| 90 | $C_3H_6OCOCH_2Cl$ | $CH_3$ | violet |
| 91 | $C_3H_6OCOCH_2OC_6H_5$ | $CH_3$ | violet |
| 92 | $C_2H_4OCOCH_2C_6H_5$ | $CH_3$ | violet |
| 93 | $C_3H_6OCOCH_2C_6H_5$ | $C_2H_5$ | blue violet |
| 94 | $C_3H_6OCOC_2H_4Cl$ | $CH_3$ | violet |
| 95 | $C_2H_4OCOC_2H_4Cl$ | $CH_3$ | violet |
| 96 | $C_2H_4OCOC_3H_6Cl$ | $CH_3$ | violet |

-continued

| Example | R | R¹ | Fluorescence in ethanol |
|---|---|---|---|
| 97 | $C_2H_4O-\overset{O}{\underset{\|}{C}}-OCH_3$ | $CH_3$ | violet blue violet |
| 98 | $C_3H_6O-\overset{O}{\underset{\|}{C}}-OC_2H_5$ | $C_2H_5$ | |
| 99 | $C_2H_4O\overset{O}{\underset{\|}{C}}-OC_4H_9$ | $CH_3$ | violet |
| 100 | $C_2H_4O\overset{O}{\underset{\|}{C}}-OC_6H_{13}$ | $C_2H_5$ | blue violet |
| 101 | $C_3H_6O-\overset{O}{\underset{\|}{C}}-OC_8H_{17}$ | $C_4H_9$ | blue violet |
| 102 | $C_2H_4O-\overset{O}{\underset{\|}{C}}-OC_2H_4OCH_3$ | $CH_3$ | violet |
| 103 | $C_2H_4O-\overset{O}{\underset{\|}{C}}-OC_2H_4OC_4H_9$ | $C_2H_5$ | blue violet |
| 104 | $C_2H_4O-\overset{O}{\underset{\|}{C}}-NHCH_3$ | $CH_3$ | violet |
| 105 | $C_3H_6\overset{O}{\underset{\|}{OCNHCH_3}}$ | $CH_3$ | violet |
| 106 | $C_2H_4O\overset{O}{\underset{\|}{C}}-NHC_2H_5$ | $C_4H_9$ | blue violet |
| 107 | $C_2H_4O\overset{O}{\underset{\|}{C}}-NHC_3H_7$ | $CH_3$ | violet |
| 108 | $C_3H_6O\overset{O}{\underset{\|}{C}}-NHC_4H_9$ | $C_2H_5$ | blue violet |
| 109 | $C_3H_6O\overset{O}{\underset{\|}{C}}-NHC_6H_{13}$ | $CH_3$ | violet |
| 110 | $C_2H_4O\overset{O}{\underset{\|}{C}}-NHC_8H_{17}$ | $CH_3$ | violet |
| 111 | $(C_2H_4O)_2H$ | $CH_3$ | violet |
| 112 | $(C_2H_4O)_3CH_3$ | $C_5H_{11}$ | blue violet |
| 113 | $(C_2H_4O)_2C_2H_5$ | $C_4H_9$ | blue violet |
| 114 | $(C_2H_4O)_2C_4H_9$ | $CH_3$ | violet |
| 115 | $(C_2H_4O)_3C_4H_9$ | $CH_3$ | violet |
| 116 | $(C_3H_6O)_3CH_3$ | $CH_3$ | violet |
| 117 | $CH_2-CH-CH_2\ OCH_3$ <br> $\quad\quad\ \ \|$ <br> $\quad\quad\ \ OH$ | $C_2H_5$ | blue violet |
| 118 | $CH_2-CH-CH_2OC_4H_9$ <br> $\quad\quad\ \ \|$ <br> $\quad\quad\ \ OH$ | $C_2H_5$ | blue violet |
| 119 | $CH_2-CH-CH_2-O-CH_2-\overset{C_2H_5}{\underset{C_4H_9}{CH}}$ <br> $\quad\quad\ \ \|$ <br> $\quad\quad\ \ OH$ | $CH_3$ | violet |
| 120 | $CH_2-CH-CH_2-OC_2H_4OCH_3$ <br> $\quad\quad\ \ \|$ <br> $\quad\quad\ \ OH$ | $C_2H_5$ | blue violet |
| 121 | $CH_2-CH-CH_2-OC_2H_4OC_4H_9$ <br> $\quad\quad\ \ \|$ <br> $\quad\quad\ \ OH$ | $C_4H_9$ | blue violet |
| 122 | $CH_2-CH-CH_2-OC_6H_5$ <br> $\quad\quad\ \ \|$ <br> $\quad\quad\ \ OH$ | $CH_3$ | violet |
| 123 | $CH_2-CH-CH_2-OC_6H_4Cl$ <br> $\quad\quad\ \ \|$ <br> $\quad\quad\ \ OH$ | $CH_3$ | violet |
| 124 | $CH_2-CH-CH_2-OC_6H_4CH_3$ <br> $\quad\quad\ \ \|$ <br> $\quad\quad\ \ OH$ | $C_4H_9$ | blue violet |
| 125 | $CH_2-CH-CH_2-OC_6H_4OCH_3$ <br> $\quad\quad\ \ \|$ <br> $\quad\quad\ \ OH$ | $CH_3$ | violet |
| 126 | $CH_2-CH-CH_2SC_6H_5$ <br> $\quad\quad\ \ \|$ <br> $\quad\quad\ \ OH$ | $CH_3$ | violet |
| 127 | $CH_3$ | $C_2H_4OH$ | blue |
| 128 | $C_2H_5$ | $C_4H_9OH$ | blue |
| 129 | $C_4H_9$ | $CH_2-$ <br> $\ \ \|$ <br> $CH-CH_3$ <br> $\quad\quad\|$ <br> $\quad\quad OH$ | blue |
| 130 | $C_4H_9$ | $C_3H_{10}OH$ | blue |
| 131 | $C_6H_{13}$ | $C_6H_{12}OH$ | blue |
| 132 | $C_7H_{15}$ | $C_2H_4OCH_3$ | blue |
| 133 | $C_8H_{17}$ | $C_2H_4OC_2H_5$ | blue |
| 134 | $C_6H_{13}$ | $C_2H_4OC_3H_7$ | blue |
| 135 | $C_6H_{13}$ | $C_2H_4OC_4H_9$ | blue |

-continued

| Example | R | R¹ | Fluorescence in ethanol |
|---|---|---|---|
| 136 | $C_4H_9$ | $C_2H_4OC_4H_9$ | blue |
| 137 | $C_2H_5$ | $C_2H_4OC_2H_5$ | blue |
| 138 | $CH_3$ | $C_4H_9OCH_3$ | blue |
| 139 | $C_2H_5$ | $C_6H_{12}OCH_3$ | blue |
| 140 | $C_4H_9$ | $(C_2H_4O)_2CH_3$ | blue |
| 141 | $CH_3$ | $(C_2H_4O)_2C_2H_5$ | blue |
| 142 | $C_2H_5$ | $(C_2H_4O)_2C_4H_9$ | blue |
| 143 | $C_2H_5$ | $(C_2H_4O)_3CH_3$ | blue |
| 144 | $C_4H_9$ | $(C_2H_4O)_4CH_3$ | blue |

We claim:
1. A compound of the formula

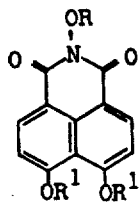

in which R is alkyl of 1 to 18 carbon atoms, allyl, cycloalkyl, cycloalkyl of 5 to 8 carbon atoms, phenylalkyl of 1 to 4 carbon atoms in the alkyl, hydroxyalkyl of 2 or 3 carbon atoms, alkoxyalkyl of 2 or 3 carbon atoms in the alkyl and 1 to 8 carbon atoms in the alkoxy, phenoxyalkyl of 2 or 3 carbon atoms in the alkyl, cyanoethyl, chloroethyl, bromoethyl, chloropropyl, bromopropyl, alkoxycarbonylethyl of 1 to 8 carbon atoms in the alkoxy, β-carbamoylethyl, alkoxycarbonylmethyl of 1 to 8 carbon atoms in the alkoxy,

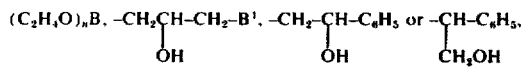

n is 2, 3 or 4; B is hydrogen or alkyl of 1 to 4 carbon atoms; B¹ is hydroxy, alkoxy of 1 to 8 carbon atoms, β-alkoxyethoxy of 1 to 4 carbon atoms in the alkoxy, phenoxy, phenoxy substituted by chloro, methyl or methoxy, phenylmercapto or methoxyphenylmercapto; and R¹ is alkyl of 1 to 6 carbon atoms, hydroxyalkyl of 2 to 6 carbon atoms, alkoxyalkyl of 1 to 4 carbon atoms in the alkoxy and 2 to 6 carbon atoms in the alkyl or $(CH_2CH_2O)_nB$.

2. A compound as claimed in claim 1 of the formula

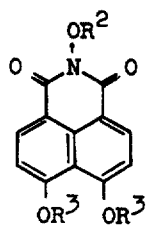

wherein
R² is alkyl of 1 to 8 carbon atoms, β-hydroxyethyl, β-hydroxypropyl, β-alkoxyethyl of 1 to 4 carbon atoms in the alkoxy, β-chloroethyl, cyclohexyl or $(C_2H_4O)_2B$, and
R³ is alkyl of 1 to 6 carbon atoms,
B having the meanings given in claim 1.
3. A compound as claimed in claim 1 of the formula

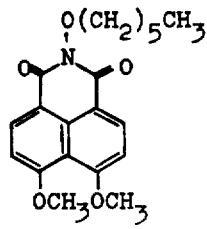

4. A compound as claimed in claim 1 of the formula

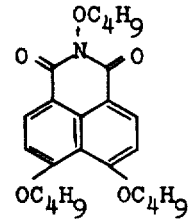

5. A compound as claimed in claim 1 of the formula

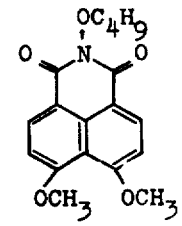

6. A compound as claimed in claim 1 of the formula

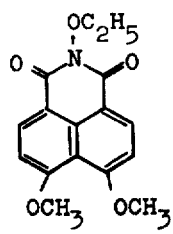

7. A compound as claimed in claim 1 of the formula

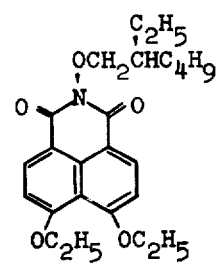

8. A compound as claimed in claim 1 of the formula
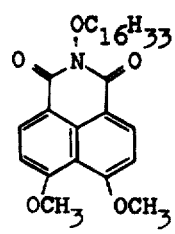
* * * * *